United States Patent [19]
Lu et al.

[11] Patent Number: 5,788,624
[45] Date of Patent: Aug. 4, 1998

US005788624A

[54] MAGNETIC THERAPY AND A MAGNETIC-FIELD SCANNING PHYSIOTHERAPEUTIC DEVICE

[75] Inventors: Hangcheng Lu; Baojun Lin; Guozhang Liu; Jing Zhao, all of Huhhot, China

[73] Assignee: Hangcheng Lu, Hohhot, China

[21] Appl. No.: 591,505

[22] PCT Filed: Jul. 28, 1994

[86] PCT No.: PCT/CN94/00057

§ 371 Date: Feb. 5, 1996

§ 102(e) Date: Feb. 5, 1996

[87] PCT Pub. No.: WO95/04572

PCT Pub. Date: Feb. 16, 1995

[30] Foreign Application Priority Data

Aug. 5, 1993 [CN] China ................. 93109226.4

[51] Int. Cl.⁶ ............................................. A61N 2/00
[52] U.S. Cl. ....................................... 600/9; 600/15
[58] Field of Search ................................. 600/9–15

[56] References Cited

U.S. PATENT DOCUMENTS 5,084,003  1/1992  Susic ............................ 600/13

FOREIGN PATENT DOCUMENTS

| | | |
|---|---|---|
| 88102352.3 | 11/1989 | China . |
| 89201090.8 | 2/1990 | China . |
| 89208486.3 | 9/1990 | China . |
| 91111260.X | 6/1992 | China . |
| 0 356 594 A1 | 3/1990 | European Pat. Off. . |
| 0 488 850 A2 | 6/1992 | European Pat. Off. . |

OTHER PUBLICATIONS

Lin et al, Geophysical Variables and Behavior, Arp. 1985, 639–649.

Stratznigg, Field Study of the Application of Static Magnetic Fields . . . , Mar. 1984, 1–14 translation pages.

*Primary Examiner*—John P. Lacyk
*Attorney, Agent, or Firm*—Fish & Richardson P.C.

[57] ABSTRACT

The present invention relates to a magnetic therapy and a physiotherapeutic device performing such a magnetic therapy. The therapy involves the application of magnetism which provides a transient penetration of magnetic flux by means of a magnetic field scanning of a whole human body or a portion thereof in a three-dimensional gradient magnetic field. The physiotherapeutic treatment device comprises (1) a bed; (2) two magnets straddling on either side of the bed; (3) a mechanical-electrical transmission system; and (4) an electric control system. Therapeutic and health-care effect is achieved by means of magnetic field scanning of the human body with the body lying on the bed facing upward while the two magnets, at properly adjusted heights and actuated by the control panel, move horizontally along the human body receiving the treatment. Clinical tests demonstrate that this invention has remarkable therapeutic effects upon the treatment of a variety of disorders.

12 Claims, 2 Drawing Sheets

000
MAGNETIC THERAPY AND A MAGNETIC-FIELD SCANNING PHYSIOTHERAPEUTIC DEVICE

TECHNICAL FIELD

The present invention relates to a magnetic therapeutic method and a magnetic-field scanning physiotherapeutic device, especially relates to a magnetic therapeutic treatment method which provides a transient penetration of magnetic flux through the human (or animal) body and performs a magnetic field scanning of the whole or partial human (or animal) body, and a physiotherapeutic treatment device of magnetic-field scanning performing the said method.

BACKGROUND OF THE TECHNOLOGY

There are a variety of treatment and health-care methods and devices which involve the application of magnetic fields to animal and human bodies, such as magnetic watches, rings, beds, vests, spectacles, belts, shoes, cushions, sofas, etc., which are available on the market and which all share the feature of applying magnetism locally on human body for treatment and health-care. Moreover, Chinese patent applications No. 88102352.3, 89201090.8, 89208486.3, 91111260.X, European patents No. 88402059.5, 91403092.9 and U.S. Pat. No. 5,084,003, etc., have all reported magnetotherapeutic devices, methods of application of magnetism to disease treatment and health-care, and their effects.

These magnetotherapeutic methods and devices available on the market and reported in technical literature have, however, all in common the following drawbacks.

1. Surface application of magnetism only, which is unable to allow the magnetic flux to penetrate deeper into the body. This is because most of the magnetic devices now available, including magnetic watches, finger-rings, beds, vests, spectacles, belts, shoes, back cushions and sofas, employ single piece magnet to apply magnetism on the surface of a portion of the body receiving treatment. If it is allowable that a magnetic field may effect treatment of the human body to a certain extent, then it can be seen that such superficial and local single piece magnet application, with only one magnetic pole facing a local surface of the human body, has, in fact, very limited effect. There have been reported some cases of local hyperemia caused by such local, stationary and prolonged application of magnetism. For example, patients wearing magnetic watches for treatment may suffer from a blue, swollen wrist, which serves to prove that a local and prolonged application of magnetism may have some adverse effect on the human body.

2. Indirect application of magnetism, which greatly reduces the effectiveness of magnetizing treatment. A typical case in point is the magnetism-treated (magnetized) drinking water for animals and human beings. Facts show that the practice of consistently drinking water that has been magnetized through appropriate magnetic treatment has some effect in the prevention and treatment of cholelithiasis and urolithiasis. However, the effect is very limited since it is achieved just by the process of magnetizing the water before drinking and allowing the water to go through the body by its circulating system, and possibly even substituting the magnetized water for the non-magnetized water within the human body. The magnetizing effect of drinking water after magnetic treatment decreases with time as the magnetizing field is taken away, which phenomenon is especially pronounced in the period immediately following the termination of magnetizing treatment.

Although some experiments show that the magnetobiological effect of treated water may last as long as 15 days, such an effect can only be of a reduced type as the magnetizing effect decreases, which just cannot compare with the magnetobiological effect of water that is magnetically treated simultaneously as it exerts its effect.

3. Local and stationary application of magnetism, which limits the scope of application of the therapy. Local application is similar to, yet different from, surface application. While surface application means the magnetic flux cannot penetrate into the body, local application means that magnetic field exists only in the region of application even if the magnetic flux could penetrate through the body, so that the magnetobiological effect can be achieved only by the natural circulation of body fluids and nervous system, etc., which brings the substances concerned under the magnetizing effect of the local stationary magnetic field and produces a magnetizing effect in the rest of the body as these substances reach there through circulation. In this sense local application is in common with the indirect application of magnetism.

DISCLOSURE OF THE INVENTION

The object of present invention is to provide a magnetic therapy and a physiotherapeutic device performing such a therapy by bringing within a short period of time into effective interaction the blood, body fluids, nervous system, channels and collaterals of the body with an appropriate magnetic field, thereby realizing a safe, reliable and effective treatment that overcomes the above mentioned drawbacks such as superficial, indirect and local nature in the application of magnetism inherent in the magnetotherapeutic devices currently available on the market.

That the present invention provides a magnetic therapy for disease treatment and health-care means that transient magnetic flux penetrates a portion of the human or animal body lying on a bed facing upward or sideward while a three-dimensional gradient magnetic field performs a reciprocal longitudinal scanning with a field intensity of 0.05–0.35 Tesla, a speed of 7.2–10.8 m/min., a longitudinal stroke of 1.8–2.2 m, to be administered once a day for a duration of 20–40 minutes for a period of 12–14 days.

The basic principle of the magnetic therapy according to the present invention is that, a charged particle when entering a magnetic field with a speed of V relative to the magnetic intensity of H will be subjected to a Lorentz force F of the magnitude of $F \propto (dH/dl)(H \times V)$, where $dH/dl$ is the magnetic field intensity gradient. The particle as acted upon by the force F will move along a spiral locus as shown in FIG. 1. The force F that the particle is subjected to is directly proportional to H, V and the magnetic field intensity gradient. Therefore, it is possible to control the force F and the motion of the charged particle by regulating H, V, and $dH/dl$. The connection of this physical phenomenon with various charged particles is one of the essential theoretical foundations of this magnetic therapy.

For instance, a large number of red blood cells in the blood contain $F^{++}$ ions, which are charged particles. When no external magnetic field is applied, the red blood cells move along blood vessels at the normal speed of blood flow. When magnets move longitudinally along the human body providing scanning, the ions such as $Fe^{++}$, $Na^+$, $Cl^-$, $K^+$ moving in the blood stream will be subjected to the action of an external magnetic field. Because of their speed relative to the magnetic field, their manner of motion will be changed from a quasi-linear motion along the blood vessels to a spiral motion with the longitudinal direction of the blood vessel as its axis, which results in three effects:

a. The blood motion of modified manner in the scanning magnetic field will exert a pressure on the internal walls of the blood vessels, thereby expand the vessels and accelerate the blood flow;

b. The superimposed chains or clusters of red blood cells that have been formed in the blood can be broken up, therefore reduce blood viscosity which has already become too great;

c. Foreign matter accumulated on the internal walls of blood vessels can be washed away, thereby prevent arteriosclerosis and thrombus.

The physiotherapeutic treatment device of the magnetic field scanning type according to present invention comprises of a bed, two magnets, a transmission system and an electric control system. Said two magnets are mounted on a support, and one of the two magnets is located above the bed while the other just beneath it, the distance between them is 250–350 mm. The N-pole of one magnet is placed opposite to the S-pole of the other one, and the other poles of both magnets are connected by a piece of magnetism-conducting iron or soft steel plate. At the bottom of the support there mounted the transmission system. The electric control system is connected with the transmission system, and it actuates the transmission system to allow a reciprocal translation of the support carrying the two magnets along the surfaces of the bed.

The embodiments and effects of the invention will be described with reference to the following drawings.

Figure 1:
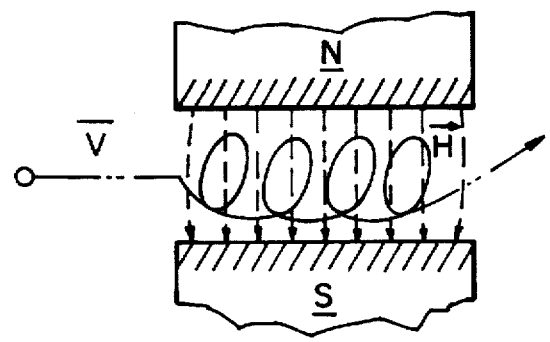
FIG. 1 Diagrammatic sketch of the locus of charged particles in magnetic field.

1. bed 2. two magnets 3. transmission system 4. electric control system 5. the human body 6. permanent magnet of NdFeB 7. iron or soft steel plate 8.seam 9. magnetism-insulating board 10. steel plate 11. caster wheel or bearing 12. guide ways 13. supporting seat

IMPLEMENT OF THE INVENTION

According to the invention, the magnetic therapy for disease treatment and health-care is that during the procedure, the transient magnetic flux will penetrate a portion of the human or animal body lying on the bed facing upward or sideward while a three-dimensinonal gradient magnetic field performs a reciprocal longitudinal scanning with a field intensity of 0.05–0.35 T, a speed of 7.2–10.8 m/min., a longitudinal stroke of 1.8–2.2 m, to be administered once a day for a duration of 20–40 minutes for a period of 12–14 days.

Experiments have proven that human beings subjected to a magnetic field of a intensity of 0.1–0.3 T will experience no change in their pulse, breathing and reflex, while the continuous action of a field intensity of 0.7 T for one hour will make people feel uncomfortable. Only after working several years in a high-intensity magnetic field will some people suffer from such symptoms as vegetable neurosis, excessive hand sweating, decelerated or accelerated heartbeat, lowered blood pressure, headache, insomnia, loss of appetite, and vestibule functional disorder, etc. It shows that as long as the field intensity is lower than 0.7 T and the application time less than one hour, there should be no problem of safety to the patient. As to the medical workers who are affected by scattered field intensity, there is no problem of safety or harm if sufficient shielding is provided against the main magnetic field and the continuous field intensity is less than the threshold level of 0.01 T.

Moreover, the present treatment applies a transient magnetic field to scan a portion of the whole body, which is quite different from the state of application wherein the human body is surrounded on all sides by a constant, strong magnetic field. This serves to illustrate further that no harm or unsafe effect will be induced in the human body if a field intensity $\leq 0.7$ T is employed for a duration of no more than one hour.

Position of the Human Body During Treatment

As mentioned above, for the sake of safety the intensity of the scanning magnetic field should be kept under 0.7 T and the duration under one hour. However, to achieve desired magnetobiological effects, the scanning time cannot be too short as only when field intensity and application time reach a certain threshold value will the magnetobiological effects be fully manifested. Therefore a mean value of 30 minutes is taken for treatment. But for a weak patient this is a fairly long time that requires a suitable body position to sustain. The standing position is too tiring and the seated position is inappropriate for magnetic penetration and field scanning. Therefore a lying position is provided for the patient. A bed is needed for the present therapy.

Meeting the Needs of Different Patients

Different patients have varied requirements for magnetic application according to their physical condition, ailments, course and category of disorders, sensibility to magnetism, etc. For example, a patient of poor health condition should receive a treatment with low field intensity, short duration or slow scanning speed, while a patient of good physical make-up and prolonged serious disorder should be given a high-intensity, long time and fast scanning treatment. In case of local disorder, such as soft tissue sprain, the patient should receive local scanning. Therefore in applying this therapy there must be control devices to regulate the magnetic field intensity, scanning speed, scanning location and scanning time for medical workers to choose and combine these parameters together.

Safety of Whole-body Application of Magnetism

Safety is the most important consideration in any healthcare treatment. The change from a surface, local, chiefly stationary and indirect application of magnetism to a whole body penetration by magnetic flux is undoubtedly a dramatic one. Therefore it is essential to give a clear-cut answer to the question of whether such a change is safe, unsafe or even harmful to the patient and the medical people administering the treatment.

Statistics show that thousands of patients all over China have been treated for over 50 disorders with magnetic therapy of the current method of magnetism application and a field intensity between 0.05–0.3 T, and there has never been an unsafe or harmful effect caused by the magnetic field. Although the application is superficial, local and stationary, its occupants are all over the body and the field intensity for safety is no greater than 0.3 T, this can provide a guideline for the safety measures to be taken for the novel magnetic therapy.

Figure 2:
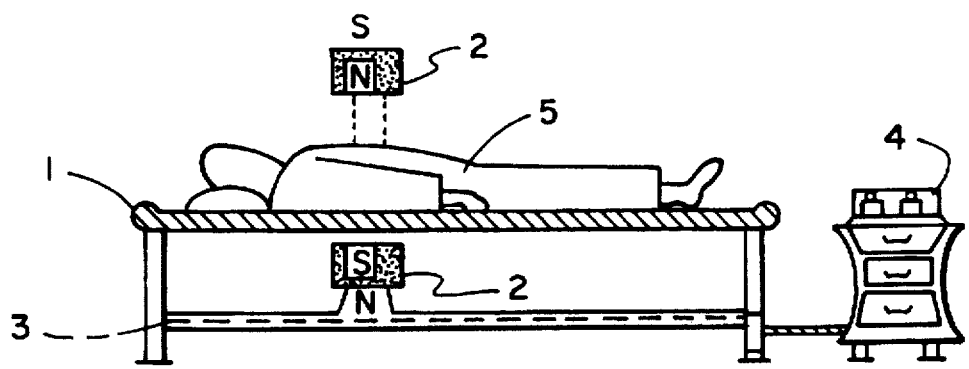
FIG. 2 Structure of the physiotherapeutic device according to present invention.
Figure 3:
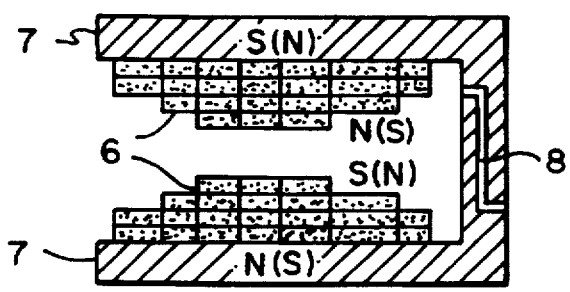
FIG. 3 Structure of the magnet, front view.
Figure 4:
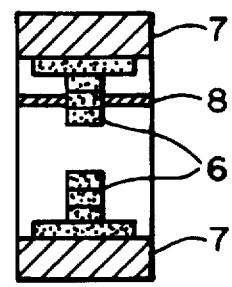
FIG. 4 Structure of the magnet, side view.
Figure 5:
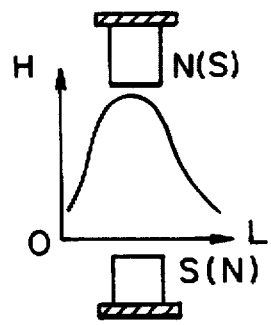
FIG. 5 Gradient distribution of the magnetic field along the longitudinal direction of the human body.
Figure 6:
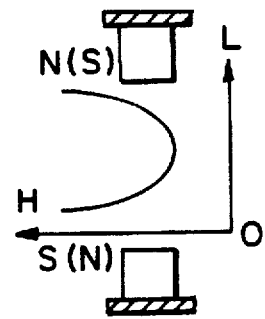
FIG. 6 Gradient distribution of the magnetic field vertically along the direction of the plumb line.
Figure 7:
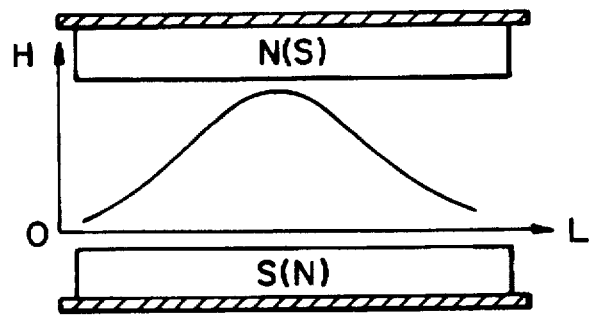
FIG. 7 Gradient distribution of the magnetic field along the transverse direction of the human body.
Figure 8:
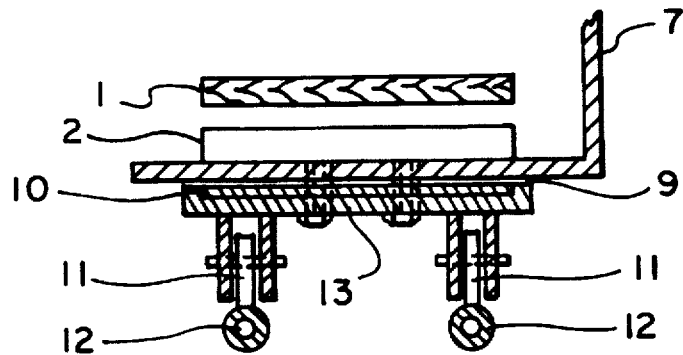
FIG. 8 Connection of the magnets with transmission mechanism.

As illustrated in FIGS. 2, 3, 8, the present invention provides a physiotherapeutic treatment device of the magnetic field scanning type which comprises a bed (1), two magnets (2), a transmission system (3) and an electric control system (4).

Said two magnets (2) are mounted on a support, and one of the two magnets (2) is located above the bed while the other just beneath it, the distance between them being 250–350 mm. The N-pole of one magnet is placed opposite to the S-pole of the other one, and the other poles of both magnets are connected by a piece of magnetism-conducting iron or soft steel plate (7).

The transmission system (3) is mounted at the bottom of said support, and may be located either below the two magnets or beneath one magnet but above the other, and is set on bracket two guide ways disposed under the bed (1).

The electric control system (4) is connected with the transmission system (3), and it actuates the transmission system (3) to allow a reciprocal translation of the two magnets (2) along the surfaces of the bed (1).

The two magnets (2) are of 600–700 mm in length, 30–50 mm in width and 70–90 mm in height, and are made either from the NdFeB and SmCo series of rare earth elements or ferrite permanent magnetic materials. The magnets(2) can also be made of electric magnets or two groups of small revolving magnetizers. Or they may each comprises a number of smaller magnetic pieces with more layers of magnets positioned in the middle and fewer layers at either end, wherein the small magnetic pieces of 40 mm×30 mm×15–30 mm (L×W×H) each are fastened by means of epoxy resin, glue No. 502 or other glues on the magnetism-conducting plate (7) which is made of two pieces of pure iron or soft steel of 920 mm×120 mm×20 mm (L×W×H) each, between the two pieces of which there is a seam (8), and which is securely surrounded on all sides by a frame of aluminum, brass, or stainless steel.

Said transmission system (3) comprises a mechanical-electrical transmission means, and a bracket. This bracket comprises a magnetism-insulating board (9), beneath the magnetismconducting plate (7), a steel plate (10) under the magnetism-insulating board (9), and a supporting seat (13) to place the steel plate (10). The magnetism-conducting plate (7), magnetism-insulating board (9) and steel plate (10) are fixed together by means of a bolt, and as an intergrated part, are set on the supporting seat (13), under which there is a caster wheel or bearing (11).

Under the bed, there disposed two steel guide ways (12) which are parallel to the bed, the caster wheel (11) of the supporting seat for transmission apparatus (3) is set on the guide ways (12) and driven to move along them by means of a variable-frequency speed-adjusted linear motor or a linear stepping motor, thus allows a reciprocal translation of the two magnets (2) along the surfaces of the bed (1).

The bed(1) comprises a bed board which may be made of wood, hard nylon, aluminum or its alloy, glass fiber reinforced plastic, or other non-conductors of magnetism, and a steel support underneath the bed board. The magnetic therapeutic device of the invention may also make use of a normal bed by some adjustment, instead of the bed board (1).

The electrical control system (4) matches the transmission system (3) in function, enabling the transmission system to realize speed variation, magnetic scanning of the whole or partial human body, as well as timing and alarm control.

The Exemplary Embodiments of the Invention are Described Below:

Embodiment 1: The upper and lower magnets are made of small permanent magnets of NdFeB with a (BH)max=N30, which are superimposed in layers and connected in series to form two magnetic bodies each with a length×width×height=700 mm×30 mm×70 mm, the N-pole of one body faces the S-pole of the other body. Direction of the length of the magnets is vertical to the longitudinal axis of the bed while its height is parallel to the plumb line. The magnetic bodies are fastened by a magnetism-conducting support on either side of the bed. The support can be adjusted to provide an adjustment of the relative distance between the two magnetic bodies. The upper and lower magnets move simultaneously at a speed of 7.2 m/min, parallel to the bed reciprocally with a stroke of 1.8 m. The scanning time required for treatment, scanning speed, field intensity and scanning location are all controlled by the electric control panel. The field intensity range selected is 0.08–0.1 T at body surface and 0.01–0.03 T inside the body. A 14-day treatment of 30 minutes daily forms a therapeutic period.

Embodiment 2: The size of the two superimposed magnet bodies is 700 mm×30 mm×75 mm (L×W×H) each. The range of adjustable field intensity is 0.15–0.25 T at body surfaces and 0.01–0.05 T inside. The rest is the same as Embodiment 1.

Embodiment 3: All the structure and relevant parameters are the same as in Embodiment 2, except that the driving power for the magnetic poles is provided by a frequency-variable speed-adjusted motor and electric control is realized by a microcomputer numerical control system, thus forming a mechanical-electrical unity.

Embodiment 4: The structure is the same as in Embodiment 2, except that the upper and lower magnetic bodies are replaced by two rows of equal length of small revolving magnetizers with reverse poles facing each other. The scanning magnetic field in this case is revolving as it moves forward and backward.

Embodiment 5: The upper and lower magnetic bodies are replaced by groups of small electric magnets densely placed in a matrix-like fashion of the same size as that of the bed and parallel to the bed. A microcomputer controls the connection and disconnection of electrical coils for the magnets to form a pulsating magnetic field along the direction of the plumb line. This pulsating field may scan the whole body by moving longitudinally back and forth, or it may form a continuous or discontinuous pulsating field at any particular location as required by the treatment. This manner is especially suitable for treating channels, collaterals and acupoints in traditional Chinese medicine theory.

Embodiment 6: Replace the two magnetic bodies with ferrite or other permanent magnets or electromagnetic materials. The other structures and relevant parameters are the same as in Embodiment 2.

Embodiment 7. The transmission system is replaced by a linear stepping motor. The rest is the same as in Embodiment 3.

Industrial Usefulness:

The advantages and positive effects of the present invention are:

1. It has overcome the common shortcomings of superficial, indirect and local application of magnetism now prevalent in the conventional magnetic treatment devices, and has thus improved by a great margin the health-care and curing effect of those disorders that can be subjected to magnetic therapy.

2. It has substituted transient scanning a portion of the body for local stationary application of magnetism employed by the conventional magnetic treatment devices. The invention activates body fluids, blood, nerves, channels and collaterals in a biological body with magnetism and then moves the magnetic field away in proper time, thereby ensuring the initial magnetizing effect on the systems concerned within the body while eliminating such side-effects produced by prolonged stationary magnetism as local hyperemia and blistering.

3. By means of scanning the magnetic field moves with a speed relative to the biological body which, from the physics point of view, is tantamount to changing the movement of charged particles within the biological body such as red blood cells from the original linear motion along the blood vessels to a spiral motion with the original linear line as its axis. This causes not only an increase of the energy and momentum of the various charged particles such as the $Cl^-$, $Na^+$ ions in and outside cell walls and $Fe^{++}$ ions in red blood cells, but also a change in the energy state of the movement of electrons outside the nuclei of these particles because of the electromagnetic induction, thereby improving ion activity and promoting biochemical and metabolic functions within the body.

4. The viscosity of blood within a human body increases with age and foreign matter may also accumulate as sediments on the walls of blood vessels with age, causing such cardiovascular disorders as arterioscleroses, thrombus, and myocardial infarction, etc., in old people. Increased blood viscosity is closely related to the formation of superimposed chains and clusters of red blood cells. Transient scanning of a portion of the body has very marked effect on the prevention and cure of senile cardiovascular disorders by reducing blood viscosity. Since such improvement is achieved by an improvement in the natural functioning of the biological body, it has no side effect caused by the action of any medicine.

5. During the procedure using the therapy of present invention, different combinations of magnetic field intensity, scanning speed, scanning time and scanning location can be chosen according to the disease course, seriousness, and physical status of the patient. So that it can be avoided that the patient feels uncomfortable at the beginning of the scanning of magnetic field, and this therapy can be used for a variety of different patients as well as different kinds of disorders.

6. The invention applies a transient magnetic field contiguously to cover a portion of the whole biological body, which is a method fundamentally different from that of placing the body inside a strong and closed magnetic field. In addition, the magnetic field intensity as employed in the invention has a gradient distribution, i.e., to a patient lying on the bed between the magnetic poles facing upward, the field intensity along the upper and lower body surfaces of the patient is relatively large, at 0.05–0.35 T (which figure is selected according to the results of a large number of animal tests as well as a large number of clinical tests of the available magnetic therapeutic devices), while inside the body near the heart the field intensity is relatively weak, at 0.01–0.05 T. Transient scanning of a portion of the whole body at this range of field intensity will have no side effect of any kind, thus ensuring absolute safety from magnetism to the patient as well as to medical personnel.

7. By applying a transient magnetic field scanning to a portion of the whole body the present invention promotes with magnetic force the activity of biological circulating particles within the body and reduces the disorder of natural functions of the body, thus providing treatment for diseases; by increasing the activity of natural functions, the invention also has a health-care effect. Therefore, patients undergoing a treatment employing this method may experience marked improvement or even cure of several disorders. No medicine is used in the therapy, which is completely in line with the goal set forth by WHO(World Healthcare Organization) to adopt natural therapy and get rid of the use of medicine by the year 2025.

We claim:

1. A method for magnetic therapy, said method comprising:

generating a magnetic field with the intensity of 0.05–0.35 Tesla;

applying the magnetic field to a human body so that the magnetic field penetrates the human body;

moving the magnetic field along the human body reciprocally at a speed of 7.2–10.8 meter/minute with a stroke of 1.8–2.2 meters, wherein the applying and moving steps last for 20–40 minutes in total per day;

repeating the generating, applying, and moving steps for 11–13 days.

2. A device for magnetic therapy, comprising:

a bed;

two magnets mounted on a support, said magnets being located above and beneath the bed, respectively; the N-pole of one magnet facing the S-pole of the other magnet; and the remaining poles of the two magnets being connected by a magnetism-conducting iron or soft steel plate;

a transmission system attached to the support, said transmission system allowing reciprocal translation of the support and the two magnets along the surfaces of the bed; and an electric control system connected to said transmission system, said control system actuating said transmission system.

3. A device according to claim 2, wherein said magnets are magnetic bars that are 600–700 mm in length, 30–50 mm in width and 70–90 mm in height, and made from a material of the NdFeB and SmCo series of rare earth elements or a ferrite permanent magnetic material.

4. A device according to claim 3, wherein said magnets each consist of a plurality of smaller magnetic pieces with more magnetic pieces positioned in the middle than at either end.

5. A device according to claim 4, wherein said smaller magnetic pieces are bar-shaped and 40 mm×30 mm×15–30 mm (L×W×H) in dimension, each of said smaller magnetic pieces being fastened by means of epoxy resin or glue No. 502 onto the magneticism-conducting plate, said plate being 920 mm×120 mm×20 mm (L×W×H) in dimension and securely surrounded on all sides by a frame of aluminum, brass, or stainless steel.

6. A device according to claim 2, wherein said magnets are electric coiled magnets or revolving magnetizers.

7. A device according to claim 2, wherein said support is located underneath the bed, and comprises a magnetism-insulating board, and said transmission system comprises a motor, and two guide ways with caster wheels or bearings, said guide ways being located underneath and parallel with the longitude of the bed, said support being connected via a chain, steel cable, or leadscrew to a transmission gearbox or a belt transmission mechanism of the motor so that it slides on said guide ways.

8. A device according to claim 2, wherein said transmission system comprises a variable-frequency speed-adjusted linear motor.

9. A device according to claim 2, wherein said transmission system comprises a linear stepping motor.

10. A device according to claim 2, wherein the bed comprises (i) a bed board made of wood, hard nylon, aluminum or an alloy thereof, or glass fiber-reinforced plastic, and (ii) a steel support beneath the bed board.

11. A device according to claim 2, wherein said electrical control system controls said transmission system, enabling said transmission system to realize speed variation, complete or partial magnetic scanning of the human body, and timing and alarm control.

12. A device according to claim 2, wherein the distance between the magnets is 250–350 mm.

* * * * *